United States Patent [19]

Meek et al.

[11] Plant 4,722

[45] May 19, 1981

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 2,035

[22] Filed: Jan. 8, 1979

[51] Int. Cl.[3] ..... A01H 5/00

[52] U.S. Cl. ..... Plt./82

[58] Field of Search ..... Plt./82

*Primary Examiner*—Robert E. Bagwill
*Assistant Examiner*—James R. Feyrer
*Attorney, Agent, or Firm*—Schwartz, Jeffery, Schwaab, Mack, Blumenthal & Koch

[57] ABSTRACT

A chyrsanthemum plant known by the cultivar name Viva and particularly characterized as to uniqueness by the combined characteristics of flat capitulum form; anemone capitulum type; red-bronze ray floret color; diameter across face of capitulum ranging from 45 to 60 mm. at maturity; uniform eight week photoperiodic flowering response to short days; tall plant height when grown as a pinched spray pot, and upright branching pattern.

4 Drawing Figures

The present invention comprises a new and distinct cultivar of *Chrysanthemum morifolium,* Ramat., hereinafter referred to by the cultivar name Viva.

Viva is a product of a planned breeding program which had the objective of creating new chrysanthemum cultivars with anemone capitulum type, with bronze ray floret color, with eight or nine week flowering response, and with the ability to produce commercially acceptable quality in year round pot mum programs. Such traits in combination were not present in previously available commercial cultivars.

Viva was originated from a cross made in a controlled breeding program in Barberton, Ohio in 1976. The female parent was #712600006 (unnamed seedling), a golden bronze anemone originated from a cross between #70038009 (unnamed seedling) and #70038014 (unnamed seedling). The male parent of Viva was #71078021 (unnamed seedling), a red-bronze daisy originated from a cross between Dramatic, disclosed in U.S. Plant Pat. No. 3,189, and Mischief (unpatented; commercially available).

Viva was discovered and selected as one flowering plant within the progeny of the stated cross by Jack M. Meek and William E. Duffett on May 2, 1977 in a controlled environment in Barberton, Ohio.

The first act of asexual reproduction of Viva was accomplished when vegetative cuttings were taken from the initial selection in June, 1977 in a controlled environment in Barberton, Ohio by a technician working under formulations established and supervised by Jack M. Meek and William E. Duffett. Continued asexual reproduction by vegetative cuttings for evaluative tests in flowering and stock programs in conjunction with horticultural examination of selected units initiated Nov. 8, 1977 has demonstrated that the combination of characteristics as herein disclosed for Viva are firmly fixed and are retained through successive generations of asexual reproduction.

Viva has not been observed under all possible environmental conditions. The phenotype may vary significantly with variations in environment such as temperature, light intensity, and day-length. The following observations, measurements, and comparisons describe plants grown in Barberton, Ohio and in Salinas, Calif. under greenhouse conditions which approximate those generally used in commercial practice. The following traits have been repeatedly observed and are determined to be basic characteristics of Viva which in combination distinguish this chrysanthemum as a new and distinct cultivar:

(1) Flat capitulum form.

(2) Anemone capitulum type.

(3) Red-bronze ray floret color, with minimal color oxidation.

(4) Diameter across face of capitulum ranging from 45 to 60 mm. at maturity.

(5) Uniform eight week photoperiodic flowering response to short days.

(6) Tall plant height (requiring 1–2 long day weeks prior to pinch and short days, and two applications 2500 ppm B-9 SP 14 to 21 days after the beginning of short days to attain a flowered plant height of 30 to 45 cm.).

(7) Upright branching pattern.

The accompanying photographic drawings show typical inflorescence and foliage characteristics of Viva. Sheet 1 is a color photograph of the inflorescence of Viva. Some degree of difficulty was encountered in obtaining accurate color representation, with the depicted color being more blue or less red and lighter in intensity than the actual ray floret color. The color readings as specified within the disclosure text are, however, correct. Sheet 2 is a black and white photograph of three views of the capitulum of Viva. Sheet 3 is a black and white photograph showing the foliage of Viva at three stages of growth. Sheet 4 comprises color chips which accurately depict the gradation in ray floret and disc floret colors, with the chips representing such colors under natural daylight conditions.

Of the many commercial cultivars known to the present inventors the most similar in comparison to Viva are Spark, disclosed in U.S. Plant Pat. No. 3,946, and Dramatic. Reference is made to attached Chart A which compares certain characteristics of Viva to those same characteristics of Spark and Dramatic. General comparisons are as follows:

(1) In comparison to Spark, Viva has less red (more bronze) ray floret color, more pronounced protrusion of center disc (anemone type), more upright branching pattern, larger diameter across face of capitulum, taller plant height, and longer flowering response period. The capitulum form of Viva is similar to that of Spark.

(2) In comparison to Dramatic, Viva has more red (less yellow) ray floret color, different capitulum type, more upright branching pattern, smaller diameter across face of capitulum, and shorter flowering response period. The capitulum form and plant height of Viva are similar to those same characteristics of Dramatic.

In the following description, color reference is made to A Limit Color Cascade, by the Munsell Company, 1972 edition. The color values were determined between 2:30 and 3:00 P.M. on Nov. 20, 1978 under 100 foot-candle light intensity (incandescent light source) at Salinas, Calif.

Botanical classification: *Chrysanthemum morifolium,* Ramat., cv Viva.

I. Inflorescence:

A. *Capitulum.*—Form: flat. Type: anemone. Diameter across face: 45 to 60 mm.

B. *Corolla of ray florets.*—Color (General Tonality at a distance of three (3) meters): approximately 35-14 to 35-13. Color (abaxial): 38-14 to 38-15, oxidizing with age to 36-13 to 36-14. Persistence: resists shatter.

C. *Corolla of disc florets.*—Shape: elongated (anemone type). Color (abaxial): 35-14. Color (adaxial): 27-3 overlaid with 35-14.

D. *Reproductive organs.*—Androecium: present disc florets only; scant to few; scant pollen. Gynoecium: present both ray and disc florets.

II. Plant:

A. *General appearance.*—Branching pattern: upright. Height: tall (pot culture); responsive to B-9 SP for height control.

B. *Foliage.*—Color (abaxial): approximately 20-14. Color (adaxial): approximately 20-13 overlaid with white.

CHART A

COMPARISON OF VIVA, SPARK AND DRAMATIC.

| Cultivar | Ray Floret Color | Capitulum Form And Type | Branching Pattern | Diameter Across Face Of Capitulum | Plant Height | Flowering Response period |
|---|---|---|---|---|---|---|
| Viva | Red-bronze | Flat anemone | Upright | 45 to 60 mm. | Tall | 8 week |
| Spark | Red | Flat daisy (crested anemone) | Semi-spreading | 40 to 55 mm. | Medium | 7 week |
| Dramatic | Golden bronze | Flat daisy | Semi-upright | 60 to 90 mm. | Tall | 9 week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant known by the cultivar name Viva, as illustrated and described, and particularly characterized as to uniqueness by the combined characteristics of flat capitulum form; anemone capitulum type; red-bronze ray floret color, with minimal color oxidation; diameter across face of capitulum ranging from 45 to 60 mm. at maturity; uniform eight week flowering response; tall plant height, and upright branching pattern.

* * * * *

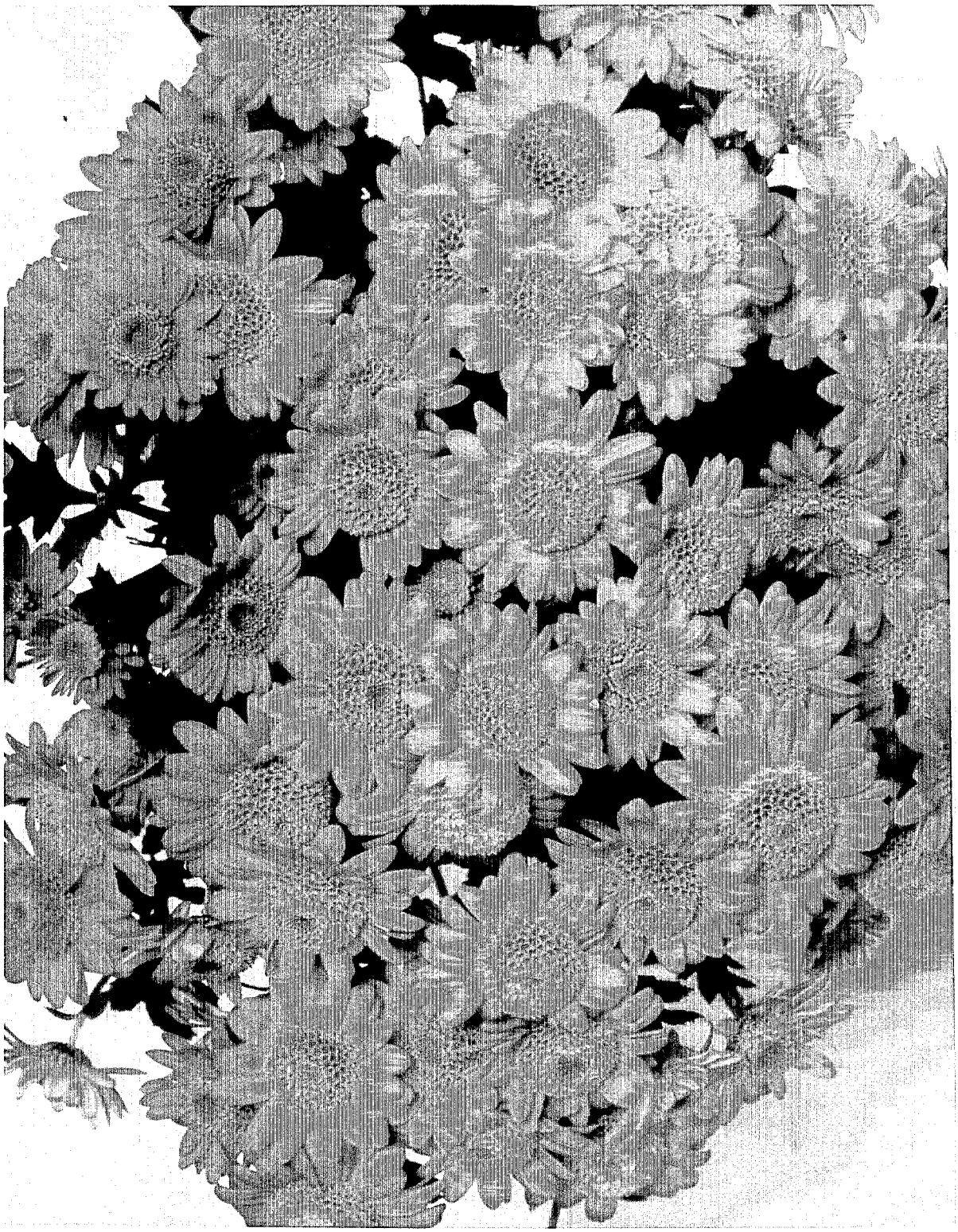

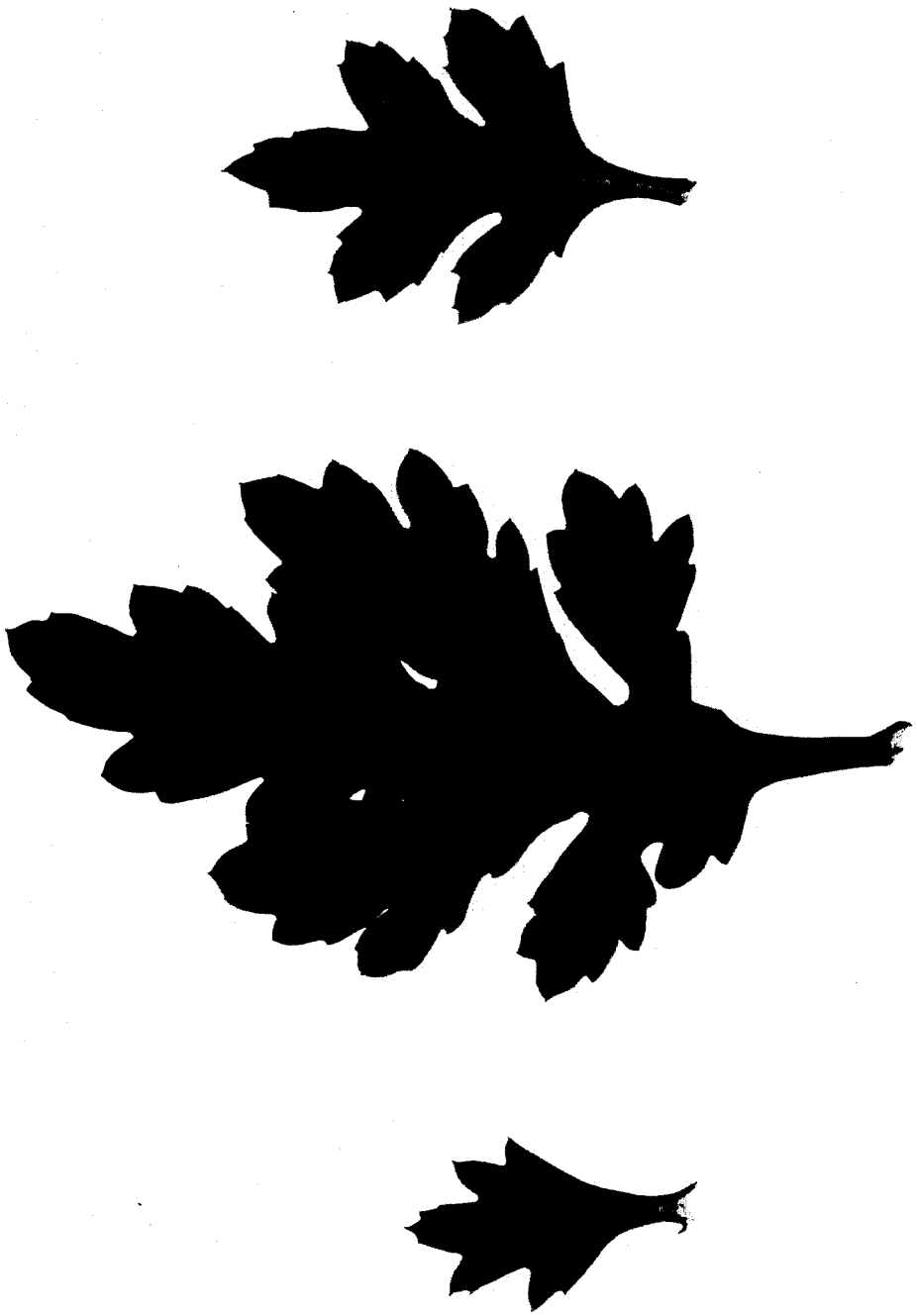

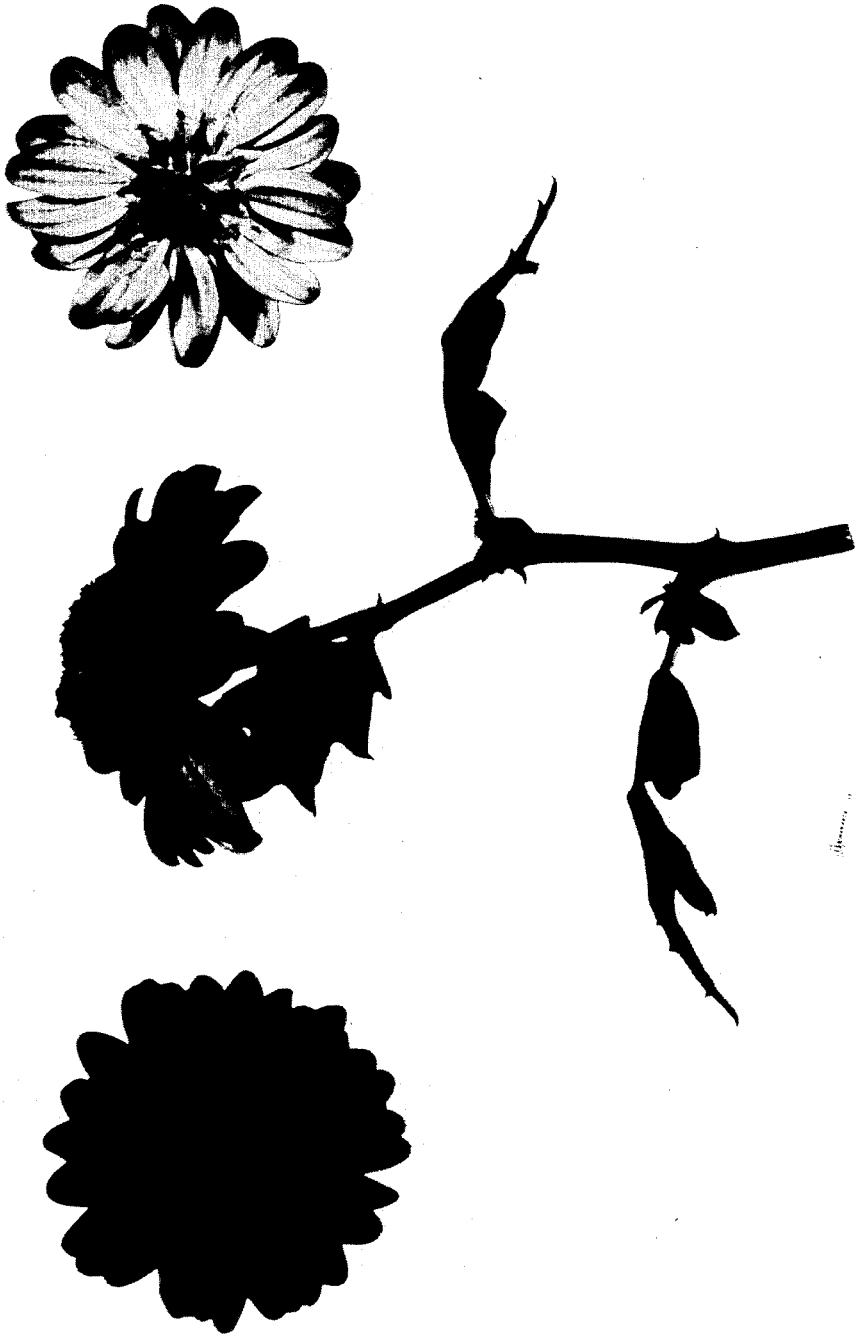

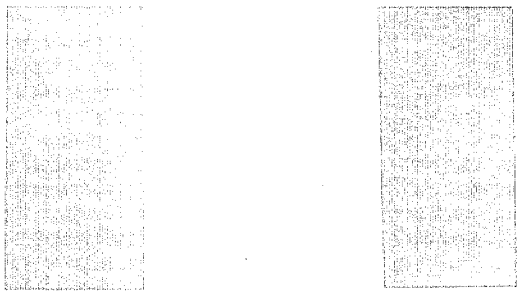

GRADATIONS OF RAY FLORET COLOR IN VIVA
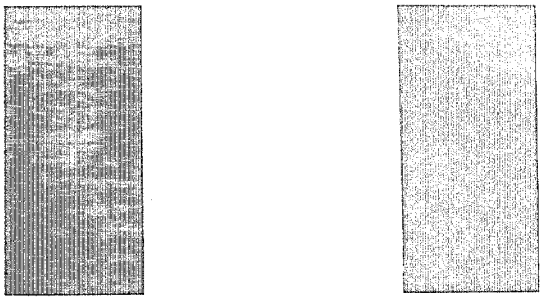
GRADATIONS OF DISC FLORET COLOR IN VIVA